United States Patent [19]

Vorbrueggen

[11] 4,169,943

[45] Oct. 2, 1979

[54] PROCESS FOR THE PREPARATION OF AMINO DERIVATIVES OF N-HETEROCYCLES

[75] Inventor: Helmut Vorbrueggen, Berlin, Fed. Rep. of Germany

[73] Assignee: Schering Aktiengesellschaft, Berlin and Bergkamen, Fed. Rep. of Germany

[21] Appl. No.: 796,278

[22] Filed: May 12, 1977

[30] Foreign Application Priority Data

May 13, 1976 [DE] Fed. Rep. of Germany ....... 2621645

[51] Int. Cl.² .............................................. C07H 19/06
[52] U.S. Cl. ........................................ 536/23; 544/69; 544/229; 536/24; 536/26; 544/124; 544/323; 546/14; 546/304; 546/297

[58] Field of Search ............................. 536/23, 24, 26; 260/239.87, 429; 544/124; 546/300

[56] References Cited

U.S. PATENT DOCUMENTS

| | | | |
|---|---|---|---|
| 3,354,160 | 11/1967 | Duschinsky et al. | 536/23 |
| 3,891,623 | 6/1975 | Vorbruggen et al. | 536/23 |
| 4,024,143 | 5/1977 | Schuman et al. | 536/23 |

*Primary Examiner*—Johnnie R. Brown
*Attorney, Agent, or Firm*—Millen & White

[57] ABSTRACT

A process for the preparation amino derivatives of N-heterocycles comprises reacting a hydroxy-N-heterocycle with hexamethylcyclotrisilazane (HTS) and/or octamethylcyclotetrasilazane (OTS) and then with $NH_3$, or a primary or secondary amine, especially in the presence of a Lewis acid.

12 Claims, No Drawings

PROCESS FOR THE PREPARATION OF AMINO DERIVATIVES OF N-HETEROCYCLES

BACKGROUND OF THE INVENTION

DOS's (German Unexamined Laid-Open Applications) Nos. 2,122,991; 2,157,036; 2,163,873; and 2,441,484, and U.S. application Ser. No. 608,250, filed Aug. 27, 1975, now U.S. Pat. No. 4,090,021, describe the conversion of hydroxy-N-heterocycles into monomeric, soluble and frequently volatile O-trimethylsilyl-N-heterocycles by silylation with hexamethyldisilazane (HMDS) and/or trimethylsilyl chloride/pyridine or triethylamine. Related art is disclosed by H. Vorbrueggen in U.S. Pat. No. 3,983,104, incorporated herein by reference. Reactive alcoholic or phenolic hydroxy and/or phosphate groups simultaneously present in the molecule are also silylated during the reaction and thus are blocked.

Reaction of a thus-substituted, silylated or free hydroxy-N-heterocycle with ammonia, or a primary or secondary amine in the presence of excess HMDS and a Lewis acid results, after several hours of heating to 80°–160° C., in high yields of aminated products. If other reactive groups are present, e.g., a ribose residue in a nucleoside, it is merely necessary following the amination to remove O-trimethylsilyl groups on the hydroxy groups of the sugar and/or of the phosphoric acid residue by transsilylation with methanol.

U.S. Pat. No. 3,884,957 teaches conversion of aromatic and aliphatic carboxylic acids to their respective nitriles by reaction with hexamethyldisilazane (HMDS), hexamethylcyclotrisilazane (HTS), and octamethylcyclotetrasilazane (OTS) by heating to 200°–230° C. in the presence of a Lewis acid, e.g., $AlCl_3$ and $ZnCl_2$.

SUMMARY OF THE INVENTION

This invention relates to a process for conversion of a hydroxy-N-heterocycle to an amino-N-heterocycle by reacting a corresponding hydroxy-N-heterocycle with an amine of Formula I

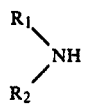

wherein $R_1$ and $R_2$ are hydrogen or an aliphatic, araliphatic, cycloaliphatic, heterocyclic, or aromatic hydrocarbyl; or $R_1$ and $R_2$ collectively, including the nitrogen atom to which they are attached, are a ring of 4, 5, 6, or 7 members; in the presence of a Lewis acid, and by conducting the reaction in the presence of hexamethylcyclotrisilazane or octamethylcyclotetrasilazane.

This invention therefore relates to a process for the conversion of the hydroxy group of a C-hydroxy-N-heterocyclic aromatic amine to an amino group, which comprises the steps of (a) silylating a C-hydroxy-N-heterocyclic aromatic amine to produce a bisdimethylsilyloxy ester of the hydroxy group, and (b) reacting the bisdimethylsilyloxy ester with ammonia or a primary or secondary amine.

DETAILED DESCRIPTION

The reaction can be represented by the following equations for the reaction of 2-pyridone or inosine and OTS:

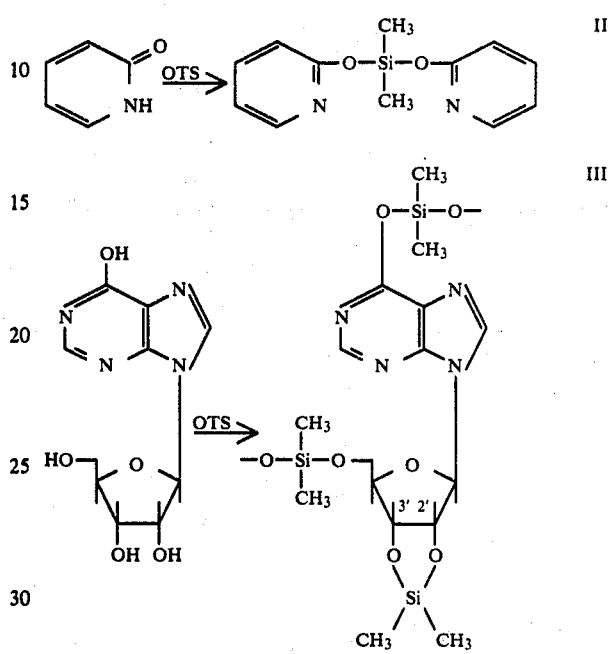

Reaction of a hydroxyheterocyclic compound with HTS and OTS always yields dimers and/or polymers. Also, hydroxy groups in the 2'- and 3'- position of inosine can be further linked intramolecularly to hydroxy groups of another ribose by dimethylsilyl groups.

Owing to formation of dimers and polymers, the size of the

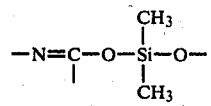

grouping to be reacted during the amination is significantly larger than a $-O-Si(CH_3)_3$-group, so that attack of the amine on the iminosilyl ether C-atom becomes more difficult. Surprisingly, this steric effect is compensated for by the improved properties manifested by the structure

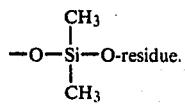

Amination takes place to give yields which are at least comparable to those obtained when HMDS is used.

Furthermore, it seems unimportant that dimers such as II react during amination with $R_1-NH-R_2$ (I) to form an initial amination product IV and a by-product V,

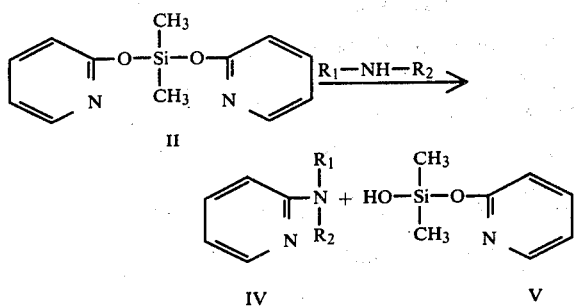

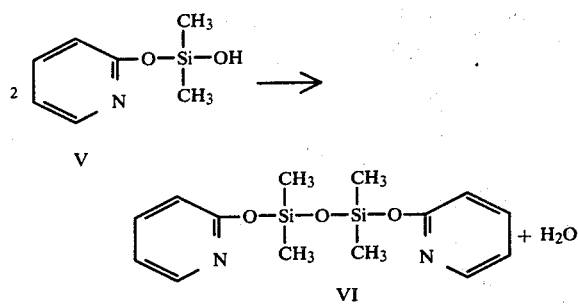

which is immediately dimerized to VI and H₂O. Therefore, with each amination step Therefore, with each amination step the size of the leaving group is increased and the attack of the amine becomes more difficult.

The silicone oil which is ultimately formed during the amination can be readily removed at the end of the reaction by extraction with pentane and/or hexane. Alternatively, the basic amination products can be easily extracted with acids.

HTS and OTS are technically readily available from (CH₃)₂SiCl₂ and NH₃. See, Inorganic Synthesis, V, 61. Each has a much higher boiling point (HTS 188° C.; OTS 225° C.) than HMDS (b.p. 128° C.), so that higher reaction temperatures can be obtained using these amines.

Utilization of HTS and OTS gives a much shorter reaction time owing to a higher reaction temperature (190°-200° C. in the case of HTS and 200°-240° C. in the case of OTS). Thus, more economical amination is attained than when HMDS is used, particularly for amination of thermally stable hydroxy heterocycles.

Because manufacturing costs for HMDS, HTS, and OTS are the same, the latter compounds are far superior to HMDS for many amination processes.

This is especially true for amination of hydroxyheterocycles which are difficult to react, such as 2-pyridone, which otherwise can be reacted only with difficulty or not at all. See, reactivity scale on page 266 in R. G. Shepherd and I. L. Fedrick, Reactivity of Amines with Nucleophiles, Advances in Heterocyclic Chemistry 4: 145 (1965).

The term "C-hydroxy-N-heterocyclic aromatic amine" as used herein means a compound having from 1-3 fused or separate rings and having as hetero ring members from 1 to 4 amino nitrogen atoms, and having a hydroxy group on a ring carbon atom of an aromatic ring bearing an amino ring member. The foregoing heterocycles can also contain a S or O atom as a ring member of the N-heterocyclic ring.

It will be understood that C-hydroxy-N-heterocyclic compounds used as starting materials frequently exist mainly in the tautomeric keto form e.g., pyridone, which can also be used in the practice of the invention.

The following hydroxy-N-heterocycles are exemplary of those which can be utilized as the starting compounds: purine nucleosides, e.g., inosine; pyrimidine nucleosides, for example, uridine and uracil; and 2 and 4-pyridone, 2 and 4-quinolone, 2 and 4-pyrimidone, 6-parabanic and cyanuric acid.

Preferred starting compounds of Formula I and accordingly the preferred products (amino derivatives of N-heterocycles), are those wherein $R_1$ and $R_2$ is the same or different and each are hydrogen or is of up to 10 carbon atoms, e.g., alkyl of 1-6 carbon atoms, cycloalkyl of 5 or 6 rings carbon atoms, e.g., cyclopentyl and cyclohexyl, carbocyclic aralkyl of 7-10 carbon atoms, e.g., benzyl and phenethyl, carbocyclic aryl, e.g., phenyl and p-tolyl, or $R_1$ and $R_2$ collectively are a divalent group of 2-6 carbon atoms in the chain, e.g., ethylene, propylene, butylene, pentamethylene or a corresponding group in which one of the carbon atoms in the chain is interrupted by one or more heteroatoms. One or more carbon atoms in the chain of the divalent group can also bear one or more simple substituents, e.g., alkyl, preferably methyl, halogen, preferably chloro or aryl, preferably phenyl.

The reaction is normally conducted at a temperature of 130°-230° C., preferably at 145°-200° C., at atmospheric pressure or under pressure as required for the selected temperature.

It is unnecessary for purposes of the reaction according to this invention to isolate the intermediate silyl compounds. The compounds, formed in situ, can be reacted in the reaction solution simultaneously or subsequently with ammonia or an amine directly to form the corresponding amino derivative.

Examples of primary amines are: methylamine, ethylamine, propylamine, butylamine, aniline, p-anisidine, benzylamine, homoveratrylamine, tryptamine, N,N-dimethylethylenediamine, etc.

Preferred secondary amines are: dimethylamine, diethylamine, pyrrolidine, piperidine, morpholine, hexamethylenimine, and N-methylpiperazine.

The reaction with ammonia is conducted at an ammonia pressure of about 30-50 atmospheres gauge. The reaction is terminated after 20-80 hours at 0°-180° C.

Excess amine, $HNR_1R_2$, is especially preferred as solvent for the reaction. However, inert solvents are also suitable, for example toluene, xylene, chlorobenzene, anisole, dioxane, glycol dimethyl ether, pyridine, and, in the case of the more sparingly soluble silyl compounds, preferably dimethylformamide.

The reaction is conducted in the presence of a catalyst. Suitable catalysts are acidic catalysts, preferably acid, salts, salts of amines, and p-toluenesulfonic acid. The metallic salts are optionally used in the reaction with excess amine $HNR_1R_2$.

Among exemplary suitable salts are mercury (II) chloride, mercury(II)acetate, tin(IV)chloride, zinc(II)chloride, titanium (IV)chloride, and boron trifluoride etherate, which are used in combination with excess amine. Salts of amines, e.g., ammonium sulfate, β-phenethylamine hydrochloride, and homoveratrylamine hydrochloride; as well as methane or trifluoromethane sulfonic acid and p-toluenesulfonic acid are preferred.

The catalysts are employed in the reaction in amounts of 0.001 mole to 5 moles per mole of N-heterocycle, preferably, in quantities of 0.05–1 mole.

Aminated heterocycles often have important biological properties as illustrated by the following compounds which can be readily prepared by the present method:

A. Substituted 2-amino-pyridines are either drugs per se or important intermediates for morphine-type drugs:
c.f. R. Hiltmann et al, Drug Research 24, 584 (1974); E. Lescot et al, Chimie Thérapeutique 213 (1969).

In combination with L-dopa 1-(2-pyridyl)piperazine is active against morbus parkinson. (Miles Laboratories, DOS No. 2 363 614).

1-Benzyl-4-N(2-pyridyl)aminopiperidine gives on N-acylation strong new analgetics. (Boehringer Mannheim, DOS No. 2 341 965 (compare also DOS No. 2 024 350).

B. As an example of substituted 2-amino-pyrimidines is piribedil (2-pyrimidyl-piperonylpiperazine) which is an important new dopamine antagonist.

[D. S. Sweet et al, Clinical Pharmacology and Therapeutics, 1077 (1975), I. Creese, Eur. J. Pharmacology, 28, 55 (1974)].

C. 2-Piperazino-quinoline (Quipazine, Miles) is a serotonine antagonist (antinociceptive action).

R. Samanin, Psychopharmakologia, 46, 219 (1976); c.f. also M. Grabowska, J. Pharm. Pharmacol. 26, 74 (1974); B. Costall, ibid 27, 368 (1975); R. M. Quock, ibid 28, 170 (1976); A. R. Green, Neuropharmacology 15, 173 (1976).

The invention also relates to the novel dimethyl silyloxy compounds produced as intermediates in accordance with the process.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

N$^6$-(2-Phenethyl)-adenosine 2.68 g. (10 millimoles) of inosine was agitated with 5.85 g. (20 mmol) of octamethylcyclotetrasilazane, 4.85 g. (40 mmol) of phenethylamine, and 0.132 g. (1 mmol) of ammonium sulfate for 10 hours at 145° C. The light-yellow, clear solution was then combined with 100 ml. of methanol, and a small amount of tetrabutylammonium fluoride was added thereto. The reaction mixture was boiled for 30 minutes. Methanol was removed by evaporation and the residue was extracted four times in the hot state with 100 ml. portions of hexane. The hexane-insoluble residue resulted, after crystallization from methanol, in a total of 3.41 g. (92%) of pure N$^6$-(2-phenethyl)-adenosine, m.p. 165°–167° C.

EXAMPLE 2

2,4-Dibenzylaminopyrimidine 2.24 g. (20 mmol) of uracil was agitated with 6.44 g. (22 mmol) of octamethylcyclotetrasilazane, 6.43 g. (60 mmol) of benzylamine, and 0.38 g. (2 mmol) of p-toluenesulfonic acid monohydrate for 5 hours at 200° C. The orange-colored solution was boiled for 1 hour with 200 ml. of CH$_3$OH and then evaporated. The residue was chromatographed with toluene/ethyl acetate on 500 g. of Al$_2$O$_3$ (act. II neutral), resulting after recrystallization from ether/cyclohexane in a total of 4.93 g. (85%) of pure 2,4-dibenzylaminopyrimidine, m.p. 68°–70° C.

EXAMPLE 3

1-(β-D-Ribofuranosyl)-2-oxo-4-morpholino-1,2-dihydro-1,3-diazine 4.88 g. (20 mmol) of uridine was agitated with 11.7 g. (40 mmol) of octamethylcyclotetrasilazane, 3.48 g. (40 mmol) of morpholine, and 0.38 g. (2 mmol) of p-toluenesulfonic acid monohydrate for 25 hours at 145° C. The reddish-brown solution was boiled with 200 ml. of methanol for 25 hours and then evaporated. The residue was extracted in the hot state with hexane (four times with 100 ml. portions): the hexaneinsoluble residue was dissolved in ethanol, treated with carbon, and yielded in several portions from ethanol a total of 5.07 g. (81%) of crystalline 1-(β-D-ribofuranosyl)-2-oxo-4-morpholino-1,2-dihydro-1,3-diazine, m.p. 106°–108° C.

EXAMPLE 4

2-Benzylaminopyridone

A suspension of 1.9 g. (20 mmol) of 2-pyridone and 4.39 g. (15 mmol) of octamethylcyclotetrasilazane and 8.75 ml. (80 mmol) of benzylamine was combined with 0.38 g. (2 mmol) of p-toluenesulfonic acid hydrate; during this step, the mixture foamed. After gently heating with agitation to 200° C., the mixture was further heated for 40 hours at 200° C. After cooling, the mixture was briefly boiled with 100 ml. of methanol, evaporated, and taken up in 100 ml. of CH$_2$Cl$_2$. After extraction with three 50 ml. portions of ice-cold 2 N H$_2$SO$_4$ with the addition of ice-cold concentrated NaOH, the mixture was extracted 4 times with 100 ml. portions of ether and then evaporated after drying (Na$_2$SO$_4$). The thus-obtained light-yellow oil (3.9 g.) was crystallized from 150 ml. of hexane at 4° C. and yielded 0.98 g. of 2-benzylaminopyridone, m.p. 94°–95° C.

By chromatographing the evaporated mother liquors on 90 g. of Al$_2$O$_3$ (A III, neutral) in hexane (4 times, 150 ml.) and finally eluting with ether (5 times with 150 ml.), another 1.92 g. of 2-benzylaminopyridone was obtained, for a total of 2.90 g. (81%), m.p. 94°–95° C.

EXAMPLE 5

4-Benzylaminopyridine

Under agitation, 0.38 g. (2 mmol) of p-toluenesulfonic acid hydrate was added to a suspension of 1.9 g. (20 mmol) of 4-pyridone and 4.39 g. (15 mmol) of octamethylcyclotetrasilazane in 8.75 ml. (80 mmol) of benzylamine; the solution foamed during this step. After gentle heating, the temperature of the mixture was elevated to 200° C. for 15 hours and, after cooling, the mixture was briefly boiled with 120 ml. of CH$_3$OH. After evaporation, the mixture was dissolved in 100 ml. of CH$_2$Cl$_4$. The bases were extracted 3 times with 40 ml. of icecold 2 N H$_2$SO$_4$. pH was brought to 9 by adding ice-cold, concentrated NaOH. Extraction of the turbid alkaline solution with 4 times 75 ml. of ether, drying (Na$_2$SO$_4$), and carbon treatment yielded, upon evaporation, 3.9 g. of a crude product which produced from 200 ml. of hexane by cooling and concentration in three portions a total of 2.81 g. (76.35%) of 4-benzylaminopyridine, m.p. 108°–110° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the conversion of the hydroxy group of a C-hydroxy-N-heterocyclic aromatic amine to an amino group, which comprises the steps of
   (a) silylating, at 130°–230° C., with hexamethylcyclotrisilazane or octamethylcyclotrisilazane, a C-hydroxy-N-heterocyclic aromatic amine to produce a bisdimethylsilyloxy ester of the hydroxy group, which aromatic amine having 1-3 fused or separate rings; having as hetero ring members 1-4 amino nitrogen atoms and 0-1 O or S atom in the N-hetero ring, and having a hydroxy group on a ring carbon atom of an aromatic ring bearing an amino ring member, and
   (b) reacting the thus-produced bisdimethylsilyloxy ester with ammonia or a primary or secondary amine of the formula

wherein $R_1$ and $R_2$ are the same or different and each is hydrogen or is alkyl of 1-6 carbon atoms, cycloalkyl of 5-6 carbon atoms, carbocyclic phenalkyl of 7-10 carbon atoms, phenyl or p-tolyl; or $R_1$ and $R_2$ collectively form an alkylene group of 2-6 carbon atoms, or a corresponding group in which one of the carbon atoms is replaced by an O or N atom, or one of the carbon atoms in the alkylene chain is substituted by methyl, halogen or phenyl.

2. The process of claim 1, wherein the C-hydroxy-N-heterocyclic amine is pyridone.
3. The process of claim 1, wherein the C-hydroxy-N-heterocyclic amine is inosine.
4. The process of claim 1, wherein the C-hydroxy-N-heterocyclic amine is uridine.
5. The process of claim 1, wherein the bisdimethylsilyloxy ester is reacted with benzylamine or phenethyl amine.
6. The process of claim 1, wherein the bisdimethylsilyloxy ester is reacted with morpholine.
7. The process of claim 1, wherein the C-hydroxy-N-heterocyclic compound is silylated with octamethylcyclotetrasilazane.
8. The process of claim 1, wherein steps (a) and (b) are conducted without isolation of the intermediately produced bisdimethylsilyloxy ester.
9. The process of claim 1, wherein the C-hydroxy-N-heterocyclic aromatic amine is pyridone, inosine, uridine or uracil and the bisdimethylsilyloxy ester is reacted with benzylamine, phenethylamine or morpholine.
10. The process of claim 9, wherein the C-hydroxy-N-heterocyclic aromatic amine is pyridone, inosine or uracil and the bisdimethylsilyloxy ester is reacted with benzylamine, phenethylamine or morpholine.
11. The process of claim 1, wherein the C-hydroxy-N-heterocyclic compound is silylated with hexamethylcyclotrisilazane.
12. The process of claim 1, wherein step (b) is conducted in the presence of excess of the primary or secondary amine or in the presence of a solvent which is inert to the reaction medium, and in the presence of a catalyst of ammonium sulfate, β-phenethylamine hydrochloride, homoveratrylamine hydrochloride, methane or trifluoromethane sulfonic acid or p-toluenesulfonic acid.

* * * * *